US011446078B2

(12) United States Patent
Millis et al.

(10) Patent No.: US 11,446,078 B2
(45) Date of Patent: Sep. 20, 2022

(54) ELECTROSURGICAL WAVE GENERATOR

(71) Applicant: Megadyne Medical Products, Inc., Draper, UT (US)

(72) Inventors: Roger Millis, West Jordan, UT (US); Ryan D. Lewis, Cedar Hills, UT (US); Paul R. Borgmeier, Salt Lake City, UT (US); Darcy W. Greep, Herriman, UT (US); Chad S. Frampton, American Fork, UT (US)

(73) Assignee: Megadyne Medical Products, Inc., Draper, UT (US)

(*) Notice: Subject to any disclaimer, the term of this patent is extended or adjusted under 35 U.S.C. 154(b) by 500 days.

(21) Appl. No.: 15/213,163

(22) Filed: Jul. 18, 2016

(65) Prior Publication Data

US 2017/0020598 A1    Jan. 26, 2017

Related U.S. Application Data

(60) Provisional application No. 62/194,390, filed on Jul. 20, 2015.

(51) Int. Cl.
*A61B 18/12* (2006.01)
*A61B 18/14* (2006.01)
(Continued)

(52) U.S. Cl.
CPC .......... *A61B 18/1206* (2013.01); *A61B 90/53* (2016.02); *A61B 18/1445* (2013.01);
(Continued)

(58) Field of Classification Search
CPC ........ A61B 18/1206; A61B 2050/3014; A61B 2560/0431; A61B 2018/00601; A61B 2018/00726; A61B 18/14
See application file for complete search history.

(56) References Cited

U.S. PATENT DOCUMENTS 3,952,748 A    4/1976   Kaliher et al.
4,017,745 A    4/1977   McMahon
(Continued)

FOREIGN PATENT DOCUMENTS

CA    2731002    2/2011
EP    2353533    8/2011
(Continued)

OTHER PUBLICATIONS

International Search Report and Written Opinion for application No. PCT/US16/42969 dated Sep. 22, 2016.
http://www.ligermedical.com/products.html; ESU-110 Electrosurgical Generator; ECU-110 Electrocautery Generator; Liger Medical, LLC; 2014.

*Primary Examiner* — Linda C Dvorak
*Assistant Examiner* — Annabeth E Rodriguez
(74) *Attorney, Agent, or Firm* — Workman Nydegger

(57) ABSTRACT

A portable, battery powered electrosurgical wave generator is usable in performing electrically driven medical procedures. The wave generator can be small and lightweight to enable a user to carry and use the wave generator in non-operating room type settings. The wave generator can include a control unit that generates output signals in each of a cutting mode, coagulation mode, and a bipolar mode. The control unit can use a single circuit structure to generate the output signals for the cutting, coagulation, and bipolar modes. The output signals can be generated solely from a voltage produced by an incorporated battery within the generator.

32 Claims, 6 Drawing Sheets

(51) Int. Cl.
*A61B 18/16* (2006.01)
*A61B 18/00* (2006.01)
*A61B 17/00* (2006.01)
*A61B 90/53* (2016.01)
*A61B 90/00* (2016.01)

(52) U.S. Cl.
CPC ....... *A61B 18/16* (2013.01); *A61B 2017/0019* (2013.01); *A61B 2017/00119* (2013.01); *A61B 2017/00221* (2013.01); *A61B 2017/00836* (2013.01); *A61B 2017/00889* (2013.01); *A61B 2018/00589* (2013.01); *A61B 2018/00601* (2013.01); *A61B 2018/00607* (2013.01); *A61B 2018/00726* (2013.01); *A61B 2018/00767* (2013.01); *A61B 2018/00875* (2013.01); *A61B 2018/126* (2013.01); *A61B 2018/1226* (2013.01); *A61B 2018/1286* (2013.01); *A61B 2018/1412* (2013.01); *A61B 2018/167* (2013.01); *A61B 2090/0803* (2016.02)

(56) References Cited

U.S. PATENT DOCUMENTS

| | | | |
|---|---|---|---|
| 4,024,467 A * | 5/1977 | Andrews | A61B 18/1206 606/37 |
| 4,108,181 A | 8/1978 | Saliaris | |
| 4,196,734 A | 4/1980 | Harris | |
| 4,359,052 A | 11/1982 | Staub | |
| 4,473,075 A * | 9/1984 | Rexroth | A61B 18/12 606/37 |
| 4,563,570 A | 1/1986 | Johns | |
| 4,727,874 A * | 3/1988 | Bowers | H03F 1/52 330/207 A |
| 4,878,493 A | 11/1989 | Pasternak et al. | |
| 5,099,840 A | 3/1992 | Goble et al. | |
| 5,163,937 A | 11/1992 | Zamba | |
| 5,167,660 A | 12/1992 | Altendorf | |
| 5,169,398 A | 12/1992 | Glaros | |
| 5,207,697 A | 5/1993 | Carusillo et al. | |
| 5,318,563 A | 6/1994 | Malis et al. | |
| 5,376,088 A | 12/1994 | Glaros | |
| 5,401,273 A | 3/1995 | Shipped | |
| 5,422,567 A | 6/1995 | Matsunaga | |
| 5,423,810 A | 6/1995 | Goble et al. | |
| 5,464,428 A * | 11/1995 | Hill | H05K 5/0086 600/523 |
| 5,688,265 A | 11/1997 | Citronowicz | |
| 5,792,138 A * | 8/1998 | Shipp | A61B 18/12 429/61 |
| 5,836,943 A | 11/1998 | Miller, III | |
| 5,871,481 A | 2/1999 | Kannenberg et al. | |
| 5,971,980 A * | 10/1999 | Sherman | A61B 17/22012 606/34 |
| 5,976,128 A | 11/1999 | Schilling et al. | |
| 6,039,734 A * | 3/2000 | Goble | A61B 18/1402 606/41 |
| 6,113,596 A * | 9/2000 | Hooven | A61B 18/14 606/42 |
| 6,210,408 B1 | 4/2001 | Chandrasekaran et al. | |
| 6,238,387 B1 | 5/2001 | Miller, III | |
| 6,238,388 B1 * | 5/2001 | Ellman | A61B 18/12 606/37 |
| 6,325,799 B1 | 12/2001 | Goble | |
| 6,402,742 B1 | 6/2002 | Blewett et al. | |
| 6,482,200 B2 | 11/2002 | Shippert | |
| 6,520,185 B1 * | 2/2003 | Bommannan | A61B 18/1487 128/898 |
| 6,562,031 B2 | 5/2003 | Chandrasekaran et al. | |
| 6,626,901 B1 | 9/2003 | Treat et al. | |
| 6,629,974 B2 | 10/2003 | Penny et al. | |
| 6,740,079 B1 | 5/2004 | Eggers et al. | |
| 6,843,789 B2 * | 1/2005 | Goble | A61B 18/1445 606/41 |
| 6,860,880 B2 | 3/2005 | Treat et al. | |
| 6,908,463 B2 | 6/2005 | Treat et al. | |
| 6,923,804 B2 | 8/2005 | Eggers et al. | |
| 6,936,047 B2 | 8/2005 | Nasab et al. | |
| 6,939,347 B2 | 9/2005 | Thompson | |
| 7,041,096 B2 | 5/2006 | Malis et al. | |
| 7,182,762 B2 | 2/2007 | Bortkiewicz | |
| 7,252,664 B2 | 8/2007 | Nasab et al. | |
| 7,255,694 B2 * | 8/2007 | Keppel | A61B 18/1206 606/34 |
| 7,445,619 B2 | 8/2008 | Auge, II et al. | |
| 7,458,974 B1 | 12/2008 | Hayashi et al. | |
| 7,713,269 B2 | 5/2010 | Auge, II et al. | |
| 7,793,812 B2 | 9/2010 | Moore et al. | |
| 7,801,585 B1 | 9/2010 | Weinstock | |
| 7,828,794 B2 | 11/2010 | Sartor | |
| 7,846,156 B2 | 12/2010 | Malis et al. | |
| 7,850,686 B2 | 12/2010 | Nobis et al. | |
| 7,862,565 B2 | 1/2011 | Eder et al. | |
| 7,887,534 B2 | 2/2011 | Hamel et al. | |
| 7,896,875 B2 | 3/2011 | Heim et al. | |
| 7,900,805 B2 | 3/2011 | Shelton, IV et al. | |
| 7,922,675 B2 | 4/2011 | Shin | |
| 7,922,713 B2 | 4/2011 | Geisel | |
| 7,942,874 B2 | 5/2011 | Eder et al. | |
| 8,016,820 B2 | 9/2011 | Treat et al. | |
| 8,064,988 B2 | 11/2011 | Weinstock | |
| 8,197,472 B2 | 6/2012 | Lau et al. | |
| 8,197,478 B2 | 6/2012 | Hayashi et al. | |
| 8,326,398 B2 | 12/2012 | Weinstock | |
| 8,328,802 B2 | 12/2012 | Deville et al. | |
| 8,377,059 B2 | 2/2013 | Deville et al. | |
| 8,382,748 B2 | 2/2013 | Geisei | |
| 8,382,751 B2 | 2/2013 | Gilbert et al. | |
| 8,401,667 B2 | 3/2013 | Gustus et al. | |
| 8,406,894 B2 | 3/2013 | Johnson et al. | |
| 8,406,898 B2 | 3/2013 | Wulfman | |
| 8,427,014 B2 | 4/2013 | Eckhoff et al. | |
| 8,439,939 B2 | 5/2013 | Deville et al. | |
| 8,454,590 B2 | 6/2013 | Smith | |
| 8,459,525 B2 | 6/2013 | Yates et al. | |
| 8,486,058 B1 * | 7/2013 | Hameed | A61B 18/1206 606/34 |
| 8,491,581 B2 | 7/2013 | Deville et al. | |
| 8,500,727 B2 * | 8/2013 | Aramayo | A61B 18/1402 606/34 |
| 8,512,335 B2 | 8/2013 | Cheng et al. | |
| 8,546,996 B2 | 10/2013 | Messerly et al. | |
| 8,551,088 B2 | 10/2013 | Falkenstein et al. | |
| 8,562,598 B2 | 10/2013 | Falkenstein et al. | |
| 8,568,400 B2 | 10/2013 | Gilbert | |
| 8,568,411 B2 | 10/2013 | Falkenstein et al. | |
| 8,573,461 B2 | 11/2013 | Shelton, IV et al. | |
| 8,574,229 B2 | 11/2013 | Eder et al. | |
| 8,579,894 B2 | 11/2013 | Falkenstein et al. | |
| 8,585,619 B2 | 11/2013 | Shin | |
| 8,591,437 B2 | 11/2013 | Shin | |
| 8,602,288 B2 | 12/2013 | Shelton, IV et al. | |
| 8,610,501 B2 | 12/2013 | Gilbert | |
| 8,622,274 B2 | 1/2014 | Yates et al. | |
| 8,632,525 B2 | 1/2014 | Kerr et al. | |
| 8,636,736 B2 | 1/2014 | Yates et al. | |
| 8,652,120 B2 | 2/2014 | Giordano et al. | |
| 8,657,174 B2 | 2/2014 | Yates et al. | |
| 8,663,262 B2 | 3/2014 | Smith et al. | |
| 8,664,934 B2 | 3/2014 | Krapohl | |
| 8,672,934 B2 | 3/2014 | Benamou et al. | |
| 8,688,228 B2 | 4/2014 | Johnson et al. | |
| 8,696,662 B2 | 4/2014 | Eder et al. | |
| 8,728,072 B2 | 5/2014 | Eder et al. | |
| 8,745,846 B2 | 6/2014 | Behnke, II et al. | |
| 8,749,116 B2 | 6/2014 | Messerly et al. | |
| 8,752,749 B2 | 6/2014 | Moore et al. | |
| 8,758,342 B2 | 6/2014 | Bales et al. | |
| 8,760,226 B2 | 6/2014 | Gilbert | |
| 8,764,747 B2 | 7/2014 | Cummings et al. | |
| 8,779,852 B2 | 7/2014 | Gilbert | |
| 8,825,176 B2 | 9/2014 | Johnson et al. | |
| 8,840,603 B2 | 9/2014 | Shelton, IV et al. | |

(56) References Cited

U.S. PATENT DOCUMENTS

| | | |
|---|---|---|
| 8,847,639 B1 | 9/2014 | Srivastava et al. |
| 8,849,371 B2 | 9/2014 | Weinstock |
| 8,888,770 B2 | 11/2014 | Eder et al. |
| 8,894,638 B2 | 11/2014 | Lau et al. |
| 8,914,130 B2 | 12/2014 | Wulfman |
| 8,915,910 B2 | 12/2014 | Falkenstein et al. |
| 8,945,115 B2 | 2/2015 | Gilbert et al. |
| 8,951,248 B2 | 2/2015 | Messerly et al. |
| 8,956,349 B2 | 2/2015 | Aldridge et al. |
| 8,986,302 B2 | 3/2015 | Aldridge et al. |
| 8,991,677 B2 | 3/2015 | Smith et al. |
| 8,992,555 B2 | 3/2015 | Smith et al. |
| 8,998,058 B2 | 4/2015 | Moore et al. |
| 8,998,891 B2 | 4/2015 | Garito et al. |
| 8,998,899 B2 | 4/2015 | Shilev et al. |
| 9,000,720 B2 | 4/2015 | Stulen et al. |
| 9,005,230 B2 | 4/2015 | Yates et al. |
| 9,007,786 B2 | 4/2015 | Yang et al. |
| 9,008,793 B1 | 4/2015 | Cosman, Sr. et al. |
| 9,017,355 B2 | 4/2015 | Smith et al. |
| 9,017,849 B2 | 4/2015 | Stulen et al. |
| 9,023,025 B2 | 5/2015 | Behnke, II et al. |
| 9,028,519 B2 | 5/2015 | Yates et al. |
| 9,033,970 B2 | 5/2015 | Behnke, II et al. |
| 9,039,692 B2 | 5/2015 | Behnke, II et al. |
| 9,039,693 B2 | 5/2015 | Behnke, II et al. |
| 9,039,695 B2 | 5/2015 | Giordano et al. |
| 9,050,083 B2 | 6/2015 | Yates et al. |
| 9,504,516 B2 | 11/2016 | Mattmiller et al. |
| 2001/0012934 A1 | 8/2001 | Chandrasekaran et al. |
| 2001/0027968 A1 | 10/2001 | Stuart |
| 2003/0144680 A1 | 7/2003 | Kellog et al. |
| 2003/0181898 A1 | 9/2003 | Bowers |
| 2004/0006337 A1 | 1/2004 | Nasab et al. |
| 2004/0030328 A1 | 2/2004 | Eggers et al. |
| 2004/0082946 A1 | 4/2004 | Malis et al. |
| 2004/0138654 A1* | 7/2004 | Goble ............... A61B 18/1206 606/34 |
| 2005/0010206 A1 | 1/2005 | Nasab et al. |
| 2005/0015080 A1 | 1/2005 | Ciccone et al. |
| 2005/0234442 A1 | 10/2005 | Spears |
| 2005/0283148 A1 | 12/2005 | Janssen et al. |
| 2006/0161148 A1 | 7/2006 | Behnke |
| 2006/0184164 A1 | 8/2006 | Malis et al. |
| 2006/0241589 A1 | 10/2006 | Heim et al. |
| 2006/0259034 A1 | 11/2006 | Eder et al. |
| 2006/0271041 A1 | 11/2006 | Eder et al. |
| 2007/0129726 A1 | 6/2007 | Eder et al. |
| 2007/0156137 A1 | 7/2007 | Geisel |
| 2007/0167941 A1* | 7/2007 | Hamel ............... A61B 18/1402 606/34 |
| 2007/0173808 A1 | 7/2007 | Goble |
| 2007/0185482 A1 | 8/2007 | Eder et al. |
| 2007/0250057 A1 | 10/2007 | Nobis et al. |
| 2008/0013350 A1* | 1/2008 | Goliszek ............ A61B 18/1206 363/68 |
| 2008/0082095 A1* | 4/2008 | Shores ............... A61B 18/1206 606/34 |
| 2008/0119841 A1 | 5/2008 | Geisel |
| 2008/0172052 A1 | 7/2008 | Eder et al. |
| 2008/0221565 A1 | 9/2008 | Eder et al. |
| 2008/0228179 A1 | 9/2008 | Eder et al. |
| 2009/0069799 A1 | 3/2009 | Daw et al. |
| 2009/0088811 A1 | 4/2009 | Wulfman |
| 2009/0088812 A1 | 4/2009 | Wulfman |
| 2009/0138003 A1 | 5/2009 | Deville et al. |
| 2009/0138006 A1 | 5/2009 | Bales et al. |
| 2009/0149732 A1 | 6/2009 | Weinstock |
| 2009/0171354 A1 | 7/2009 | Deville et al. |
| 2009/0182323 A1 | 7/2009 | Eder et al. |
| 2009/0209979 A1 | 9/2009 | Yates et al. |
| 2009/0209990 A1 | 9/2009 | Yates et al. |
| 2009/0240245 A1 | 9/2009 | Deville et al. |
| 2009/0240246 A1 | 9/2009 | Deville et al. |
| 2009/0240250 A1 | 9/2009 | Hayashi et al. |
| 2009/0248007 A1 | 10/2009 | Falkenstein et al. |
| 2009/0248013 A1 | 10/2009 | Falkenstein et al. |
| 2009/0248019 A1 | 10/2009 | Falkenstein et al. |
| 2009/0248020 A1 | 10/2009 | Falkenstein et al. |
| 2009/0248022 A1 | 10/2009 | Falkenstein et al. |
| 2010/0030212 A1 | 2/2010 | Aramayo |
| 2010/0076475 A1 | 5/2010 | Yates et al. |
| 2010/0130976 A1 | 5/2010 | Bystryak et al. |
| 2010/0241116 A1 | 9/2010 | Benamou et al. |
| 2010/0268220 A1 | 10/2010 | Johnson et al. |
| 2011/0022032 A1 | 1/2011 | Zemlok et al. |
| 2011/0060329 A1 | 3/2011 | Gilbert et al. |
| 2011/0071520 A1 | 3/2011 | Gilbert |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087256 A1 | 4/2011 | Wiener et al. |
| 2011/0112530 A1* | 5/2011 | Keller ................ A61B 18/14 606/42 |
| 2011/0115562 A1 | 5/2011 | Gilbert |
| 2011/0125176 A1 | 5/2011 | Yates et al. |
| 2011/0125177 A1 | 5/2011 | Yates et al. |
| 2011/0172660 A1* | 7/2011 | Bales, Jr. ........... A61B 18/1206 606/45 |
| 2011/0202058 A1 | 8/2011 | Eder et al. |
| 2011/0213354 A1 | 9/2011 | Smith |
| 2011/0278956 A1* | 11/2011 | Eckhoff ............. H02J 50/20 307/149 |
| 2011/0288543 A1 | 11/2011 | Cheng et al. |
| 2011/0288573 A1 | 11/2011 | Yates et al. |
| 2011/0295269 A1 | 12/2011 | Swensgard et al. |
| 2011/0319881 A1* | 12/2011 | Johnston ........... A61B 18/1206 606/33 |
| 2012/0022519 A1 | 1/2012 | Huang et al. |
| 2012/0071796 A1 | 3/2012 | Smith et al. |
| 2012/0071866 A1 | 3/2012 | Kerr et al. |
| 2012/0078139 A1 | 3/2012 | Aldridge et al. |
| 2012/0115005 A1 | 5/2012 | Stulen et al. |
| 2012/0116379 A1 | 5/2012 | Yates et al. |
| 2012/0136347 A1 | 5/2012 | Brustad et al. |
| 2012/0157995 A1 | 6/2012 | Deville et al. |
| 2012/0199631 A1 | 8/2012 | Shelton, IV et al. |
| 2012/0199633 A1 | 8/2012 | Shelton, IV et al. |
| 2012/0202388 A1* | 8/2012 | Selig .................. A61B 18/14 439/656 |
| 2012/0215216 A1 | 8/2012 | Friedrichs et al. |
| 2012/0265196 A1 | 10/2012 | Turner et al. |
| 2012/0310229 A1 | 12/2012 | Gregg |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2012/0316550 A1 | 12/2012 | Lau et al. |
| 2013/0018364 A1 | 1/2013 | Chernov et al. |
| 2013/0041371 A1 | 2/2013 | Yates et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0126581 A1 | 5/2013 | Yates et al. |
| 2013/0131660 A1 | 5/2013 | Monson et al. |
| 2013/0178848 A1 | 7/2013 | Gilbert et al. |
| 2013/0190757 A1 | 7/2013 | Yates et al. |
| 2013/0193189 A1 | 8/2013 | Swensgard et al. |
| 2013/0204243 A1 | 8/2013 | Newkirk |
| 2013/0282003 A1 | 10/2013 | Messerly et al. |
| 2013/0317565 A1 | 11/2013 | Weinstock |
| 2014/0005652 A1 | 1/2014 | Yates et al. |
| 2014/0018795 A1 | 1/2014 | Shilev et al. |
| 2014/0043070 A1 | 2/2014 | Gilbert |

(56) References Cited

U.S. PATENT DOCUMENTS

| | | |
|---|---|---|
| 2014/0062593 A1 | 3/2014 | Gilbert |
| 2014/0066927 A1 | 3/2014 | Brustad et al. |
| 2014/0081256 A1 | 3/2014 | Carmel et al. |
| 2014/0107640 A1 | 3/2014 | Yates et al. |
| 2014/0104028 A1 | 4/2014 | Johnston |
| 2014/0128850 A1 | 5/2014 | Kerr et al. |
| 2014/0128864 A1* | 5/2014 | Atwell ............... A61B 18/18 606/37 |
| 2014/0148799 A1 | 5/2014 | Mueller |
| 2014/0155880 A1 | 6/2014 | Benamou et al. |
| 2014/0188101 A1 | 7/2014 | Bales, Jr. et al. |
| 2014/0207124 A1 | 7/2014 | Aldridge et al. |
| 2014/0214136 A1 | 7/2014 | Liu et al. |
| 2014/0232463 A1 | 8/2014 | Gilbert |
| 2014/0254221 A1 | 9/2014 | Johnson et al. |
| 2014/0276750 A1 | 9/2014 | Gilbert |
| 2014/0276754 A1 | 9/2014 | Gilbert et al. |
| 2014/0276768 A1 | 9/2014 | Juergens et al. |
| 2014/0303612 A1 | 10/2014 | Williams |
| 2014/0358138 A1 | 12/2014 | Mattmiller et al. |
| 2014/0364844 A1 | 12/2014 | Van Wyk |
| 2014/0376269 A1 | 12/2014 | Johnson et al. |
| 2015/0005760 A1 | 1/2015 | Poulsen |
| 2015/0025521 A1 | 1/2015 | Friedrichs et al. |
| 2015/0025523 A1 | 1/2015 | Friedrichs et al. |
| 2015/0032096 A1 | 1/2015 | Johnson |
| 2015/0066022 A1 | 3/2015 | Shelton, IV et al. |
| 2015/0080868 A1 | 3/2015 | Kerr |
| 2015/0088116 A1 | 3/2015 | Wham |
| 2015/0088117 A1 | 3/2015 | Gilbert et al. |
| 2015/0088118 A1 | 3/2015 | Gilbert et al. |
| 2015/0088124 A1 | 3/2015 | Wham |
| 2015/0088125 A1 | 3/2015 | Wham |
| 2015/0088129 A1 | 3/2015 | Ganem et al. |
| 2015/0094703 A1 | 4/2015 | Zikorus et al. |
| 2015/0105701 A1 | 4/2015 | Mayer et al. |
| 2015/0105766 A1 | 4/2015 | Johnson et al. |
| 2015/0105767 A1 | 4/2015 | Johnson et al. |
| 2015/0105768 A1 | 4/2015 | Gilbert et al. |
| 2015/0119871 A1 | 4/2015 | Johnson et al. |
| 2015/0133912 A1 | 5/2015 | Schulz |
| 2015/0133913 A1 | 5/2015 | Gilbert et al. |

FOREIGN PATENT DOCUMENTS

| | | | |
|---|---|---|---|
| JP | 2000-504616 A | 4/2000 | |
| JP | 2011-098202 A | 5/2011 | |
| JP | 2011-520520 A | 7/2011 | |
| JP | 2014-094287 A | 5/2014 | |
| WO | WO 2007076413 A2 * | 7/2007 | ............. A61K 31/00 |
| WO | WO-2007076413 A2 * | 7/2007 | ............. A61K 31/00 |
| WO | 2010016259 | 2/2010 | |
| WO | 2014181077 | 11/2014 | |
| WO | 2014181078 | 11/2014 | |
| WO | 2014210136 | 12/2014 | |

* cited by examiner

ELECTROSURGICAL WAVE GENERATOR

CROSS-REFERENCE TO RELATED APPLICATIONS

This application claims priority to and the benefit of U.S. Provisional Patent Application Ser. No. 62/194,390, filed Jul. 20, 2015, entitled "Electrosurgical Wave Generator," the disclosure of which is incorporated herein by this reference.

BACKGROUND

1. Technical Field

The present disclosure relates generally to electrosurgical systems. More specifically, the present disclosure relates to electrosurgical wave generators that can be relatively small, portable, and/or provide unique radio frequency (RF) electrical energy outputs.

2. The Relevant Technology

In the area of electrosurgery, medical procedures of cutting tissue and/or cauterizing leaking blood vessels are performed by utilizing RF electrical energy. The RF energy is produced by a wave generator and transmitted to a patient's tissue through a hand-held electrode that is operated by a surgeon. The hand-held electrode delivers an electrical discharge to cellular matter of the patient's body adjacent to the electrode. The discharge causes the cellular matter to heat up in order to cut tissue and/or cauterize blood vessels.

The high temperatures involved in electrosurgery can cause thermal necrosis of the tissue adjacent the electrode. The longer tissue is exposed to the high temperatures involved with electrosurgery, the more likely it is that the tissue will suffer thermal necrosis. Thermal necrosis of the tissue can decrease the speed of cutting the tissue and increase post-operative complications, eschar production, and healing time, as well as increase incidences of heat damage to tissue away from the cutting site.

Additionally, typical electrosurgical wave generators require the surgeon or other operating room personnel to adjust various output parameters of the wave generator, such as the power level and/or the frequency of the electrical discharge to be delivered to the patient's tissue. Properly adjusting these various settings requires great knowledge, skill, and attention from the surgeon or other personnel.

Furthermore, typical electrosurgical wave generators are designed for use in traditional operating room or similar settings. For instance, typical electrosurgical wave generators require connection to an external power supply, such as a wall socket, to power the wave generator and produce the electrical discharge that is delivered to the patient's tissue. Moreover, the size and weight of typical electrosurgical wave generators limit the portability of such generators. More specifically, while such generators may be somewhat portable, they are typically large enough and heavy enough that the portability is limited to movement between adjacent operating rooms and the like, typically on a rolling cart.

The subject matter described and claimed herein, however, is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates generally to electrosurgical wave generators that can be relatively small, portable, and/or provide unique radio frequency (RF) electrical energy output. In one implementation, for instance, an electrosurgical wave generator for performing electrically driven medical procedures can include a control unit and a pulse-width-modulation controller. The control unit is configured to generate and control output signals to at least one surgical electrode that includes a working surface that is configured to cut through patient tissue. The pulse-width-modulation controller is configured to vary duty cycles of the output signal based upon an impedance detected from the patient tissue that the electrode is cutting.

In another implementation, an electrosurgical wave generator includes a control unit that is configured to generate and control output signals to a first surgical electrode and a second surgical electrode. The first surgical electrode and the second surgical electrode can be configured for use in a bipolar mode. The wave generator can also include an output control module that is configured to generate an output signal with a constant current until a particular change in impedance at the first surgical electrode and the second surgical electrode is detected.

In yet another implementation, an electrosurgical wave generator includes a control unit that is configured to generate and control output signals to at least one surgical electrode that is configured to perform coagulation during surgery. The wave generator also includes a flyback converter circuit. The flyback converter circuit can be configured to directly generate the output signals.

Another implementation includes an electrosurgical wave generator having a control unit that is configured to generate and control output signals to at least one surgical electrode for performing surgical procedures. The wave generator also includes a pulse-width-modulation controller that is configured to drive the output signals within each of a cutting mode, a bipolar mode, and a coagulation mode.

According to another example implementation, an electrosurgical wave generator includes first, second, and third electrical connections. The first electrical connection can be configured for connecting to a connector of a first electrosurgical instrument. Similarly, the second electrical connection can be configured for connecting to a connector of a second electrosurgical instrument. The third electrical connection can be configured for connecting to a connector of a return electrode. At least two of the first, second, and third electrical connections can create a cross connection configuration that prevents the simultaneous connection of all three of the first electrosurgical instrument, the second electrosurgical instrument, and the return electrode to the respective first, second, and third electrical connections.

In still another implementation, an electrosurgical wave generator can include a housing, a control unit, and a return electrode. The control unit is disposed within the housing and is configured to generate and control output signals to at least one surgical electrode for performing surgical procedures. The return electrode can be incorporated into the housing, such that the wave generator can be positioned on or strapped to a patient with the return electrode in contact with the patient during a surgical procedure to enable the safe flow of electrical energy from the patient to the wave generator via the return electrode.

A further implementation includes a portable, battery powered electrosurgical wave generator. The wave generator includes a housing having length, width, and height dimensions and a total volume that are limited to enable the wave generator to be carried and used in a non-operating room type setting. The wave generator also includes a control unit disposed within the housing. The control unit is configured to generate and control output signals to at least one surgical electrode for performing surgical procedures in each of a cutting mode, a coagulation mode, and a bipolar mode. Furthermore, the control unit uses a single circuit structure to generate the output signals for the cutting, coagulation, and bipolar modes. The wave generator also includes a battery disposed within the housing, where the output signals are generated solely from a voltage produced by the battery.

According to an exemplary method of the present disclosure, a unique electrosurgical wave generator is provided and used. The wave generator includes a housing, a control unit, and a return electrode. The control unit is disposed within the housing and generates and controls output signals to a surgical electrode. The return electrode is incorporated into the housing. The method also includes positioning the electrosurgical wave generator adjacent to a patient, such that the return electrode is in contact with the patient to enable the safe flow of electrical energy from the patient to the wave generator via the return electrode.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the present disclosure will be set forth in the description which follows, and in part will be obvious from the description, or may be learned by the implementations described herein. The features and advantages of the disclosure may be realized and obtained by means of the instruments and combinations particularly pointed out in the appended claims. These and other features of the present disclosure will become more fully apparent from the following description and appended claims, or may be learned by the practice of the implementations as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

The present disclosure relates generally to electrosurgical systems. More specifically, the present disclosure relates to electrosurgical generators that can be relatively small, portable, and/or provide unique radio frequency electrical energy output.

The following disclosure is grouped into various subsections under subheadings. The arrangement into subsections and utilization of the subheadings is for convenience of the reader only and is not to be construed as limiting in any sense. Thus, for instance, some embodiments of the present disclosure may include an individual feature from a single subsection while other embodiments include various combinations of features from one or more subsections.

Exemplary Operating System

Figure 1:
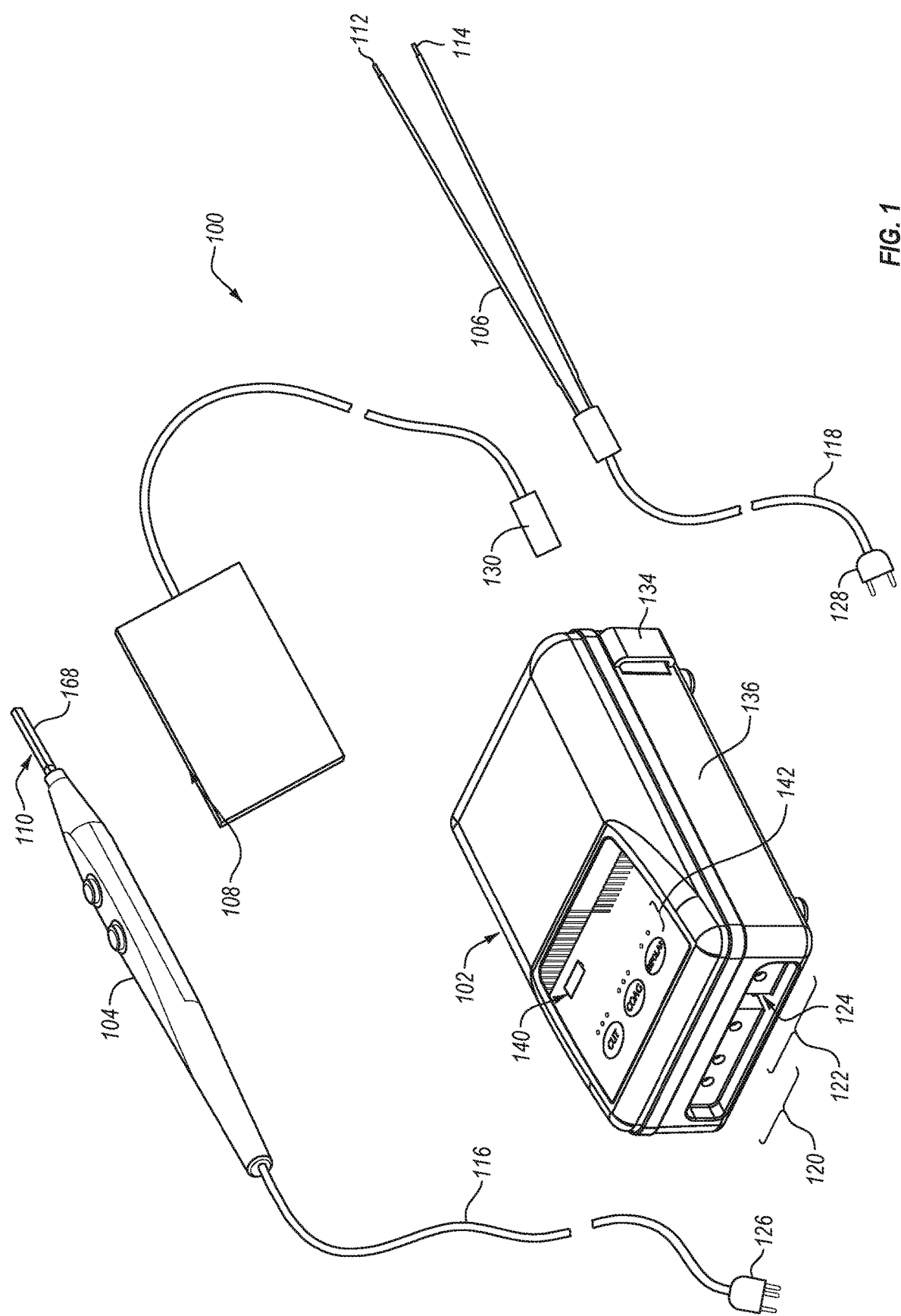
FIG. 1 illustrates an exemplary electrosurgical system according to the present disclosure.

FIG. 1 illustrates an exemplary system that can include some or all of the features of the present disclosure. In FIG. 1, an electrosurgical system 100 is illustrated, which includes a wave generator 102, a first or monopolar electrosurgical instrument 104, a second or bipolar electrosurgical instrument 106, and a return electrode 108. The wave generator 102, in one embodiment, is an RF wave generator. The first electrosurgical instrument 104 is illustrated as a hand-held electrosurgical pencil having an electrode tip 110 associated therewith. The second electrosurgical instrument 106 is illustrated as a pair of bipolar forceps with tips 112, 114. A surgeon may use either of the instruments 104, 106 in connection with the wave generator 102 during surgical procedures.

The wave generator 102 can generate an RF electrical energy wave that can be used to cut tissue and/or cauterize blood vessels during electrosurgery. Depending on various factors, including the type of procedure being performed, a surgeon may elect to use a monopolar instrument, such as instrument 104, along with a return electrode, such as return electrode 108, or may elect to use a bipolar instrument, such as instrument 106. In either case, electrical energy waves produced by the wave generator 102 can be delivered to patient tissue via the selected instrument and the circuit is completed for energy to return to the wave generator either via the selected instrument or a separate return electrode.

For instance, when the instrument 104 is electrically coupled to the wave generator 102, the electrical energy wave can power the instrument 104 and be transmitted from the wave generator 102 to the instrument 104 via a cord 116. An electrical discharge is delivered from the electrode tip 110 to the patient in order to cause the heating of cellular matter of the patient tissue that is in close contact to the electrode tip 110. The flow of radio frequency energy from the instrument 104 to the tissue results in heating of the tissue in a way that accomplishes cutting and/or coagulation as desired by the surgeon. The return electrode 108 can be electrically coupled to the wave generator 102 in order to complete the circuit and provide a return electrical path to the wave generator 102 for energy that passes into the patient's body.

Similarly, when the instrument 106 is electrically coupled to the wave generator 102, the electrical energy wave can be transmitted from the wave generator 102 to the instrument 106 via a cord 118. An electrical discharge is delivered from one of the tips 112, 114 to the patient tissue and returned to the wave generator 102 via the other tip 112, 114. Since the electrical charge is returned to the wave generator 102 via one of the tips 112, 114, there may be no need for a separate return electrode, such as return electrode 108, when the instrument 106 is used.

Cross Connection Configuration

The wave generator 102 may include electrical connections that allow for connection(s) to be made to either (i) a monopolar instrument (e.g., instrument 104) and a separate return electrode (e.g., return electrode 108), or (ii) a bipolar instrument (e.g., instrument 106) without a separate return electrode. For instance, the wave generator 102 includes an electrical connection 120 for a connector 126 associated with the instrument 104, an electrical connection 122 for a connector 128 associated with the instrument 106, and an electrical connection 124 for a connector 130 associated with the return electrode 108.

The relative position, orientation, or other features of the electrical connections 120, 122, 124 may guide a user in determining whether a return electrode (e.g., return electrode 108) should be used with the selected type of instrument (e.g., instruments 104, 106). For instance, the electrical connections 120, 122 may be positioned relative to one another and/or relative to the electrical connection 124 so that only one of the connectors 126, 128 may be connected to the wave generator 102 at a time and/or so as to either cover/block access to or leave uncovered/accessible one or more of the electrical connections 120, 122, 124.

In the illustrated embodiment, the electrical connection 120 includes three sockets that can receive the three prongs of the connector 126 associated with the instrument 104. Similarly, the illustrated electrical connection 122 includes two sockets that can receive the two prongs of the connector 128 associated with the instrument 106. It will be appreciated that the number of sockets and prongs may vary from one embodiment to another. For instance, the electrical connector 120 and the connector 126 may have fewer or more than three sockets and prongs, respectively. Likewise, the electrical connector 122 and the connector 128 may have fewer or more than two sockets and prongs, respectively.

As shown in FIG. 1, the electrical connections 120, 122 may optionally share a socket. Having the electrical connections 120, 122 share a socket may prevent both instruments 104, 106 from being electrically connected to the wave generator 102 at the same time. That is, for instance, when the instrument 104 is connected to the electrical connection 120, the instrument 106 may not be able to connect to the electrical connection 122, and vice versa. More specifically, because one of the prongs from the connector 126 is already inserted into the shared socket, one of the prongs from the connector 128 may not be inserted into the shared socket, and vice versa.

In addition or as an alternative to using a shared socket for the electrical connections 120, 122, the relative positioning of the electrical connections 120, 122, 124 may also dictate which combination of instruments 104, 106 and return electrode 108 can be connected to the wave generator 102 at the same time. By way of example, the electrical connections 120, 124 may be positioned or oriented to enable both the instrument 104 and the return electrode 108 to be connected to the wave generator 102 at the same time, while also blocking access to or otherwise preventing the instrument 106 from being connected to the wave generator 102 via the electrical connection 122.

In FIG. 1, for instance, the electrical connections 120, 124 are spaced apart from one another so that the connector 126 associated with the instrument 104 can be connected to the electrical connection 120 and the connector 130 associated with the return electrode 108 can be connected to the electrical connection 124 at the same time. As discussed above, due to the shared socket arrangement, the instrument 106 cannot be connected to the electrical connection 122 when the instrument 104 is connected to the electrical connection 120.

Additionally, the placement of the electrical connection 124 between the sockets of the electrical connection 122 can also prevent the instrument 106 and the return electrode 108 from being connected to the wave generator 102 at the same time. For instance, when the connector 128 associated with the instrument 106 is connected to the electrical connection 122 (which spans the electrical connection 124), the connector 130 associated with the return electrode 108 cannot be connected to the electrical connection 124 because the connector 126 is covering or otherwise blocking access to the electrical connection 124. Similarly, when the connector 130 associated with the return electrode 108 is connected to the electrical connection 124, the connector 128 associated with the instrument 106 cannot be connected to the electrical connection 122 because the connector 130 is blocking access to the electrical connection 122.

Thus, the electrical connections 120, 122, 124 of the wave generator 102 may have or create a cross connection configuration that allows for the instrument 104 (or other monopolar instrument) and the return electrode 108 to be connected to the wave generator 102 at the same time, while also preventing the instrument 106 (or other bipolar instrument) from being connected to the wave generator 102. The cross connection configuration can also allow for the instrument 106 (or other bipolar instrument) to be connected to the wave generator 102, while also preventing one or both of the instrument 104 (or other monopolar instrument) and the return electrode 108 from being connected to the wave generator 102 at the same time as the instrument 106.

Portability

The wave generator 102 may be designed to be highly portable so that it can be readily moved and used in a variety of locations and settings. For instance, rather than being limited to operating room type settings as with traditional electrosurgical generators, the wave generator 102 can be highly portable for use in non-traditional settings. By way of example, the wave generator 102 may be designed for use by military personnel, first responders, veterinarians, and the like, in situations that are substantially different than operating room type settings (e.g., war zones, natural disaster areas, zoos, outdoors, etc.). To enable the wave generator 102 to be highly portable and used in non-traditional settings, the wave generator 102 may include various characteristics and features that distinguish it from traditional electrosurgical generators.

By way of example, the wave generator 102 may include a battery that powers its operation rather than requiring a continuous connection to an external power source (e.g., A/C wall outlet). Powering the wave generator 102 with an incorporated battery allows the wave generator 102 to be taken to locations and used in situations where a continuous, external power source may not be available. For instance, the battery powered wave generator 102 may be taken outdoors (e.g., at zoos, at a car accident, in the mountains, on a ranch, in a war zone, etc.) where a continuous, external power source is not be available. Similarly, the battery powered wave generator 102 may be used in locations and situation where a continuous, external power source is normally available, but due to circumstances (e.g., power outages, etc.) is not.

Figure 2:
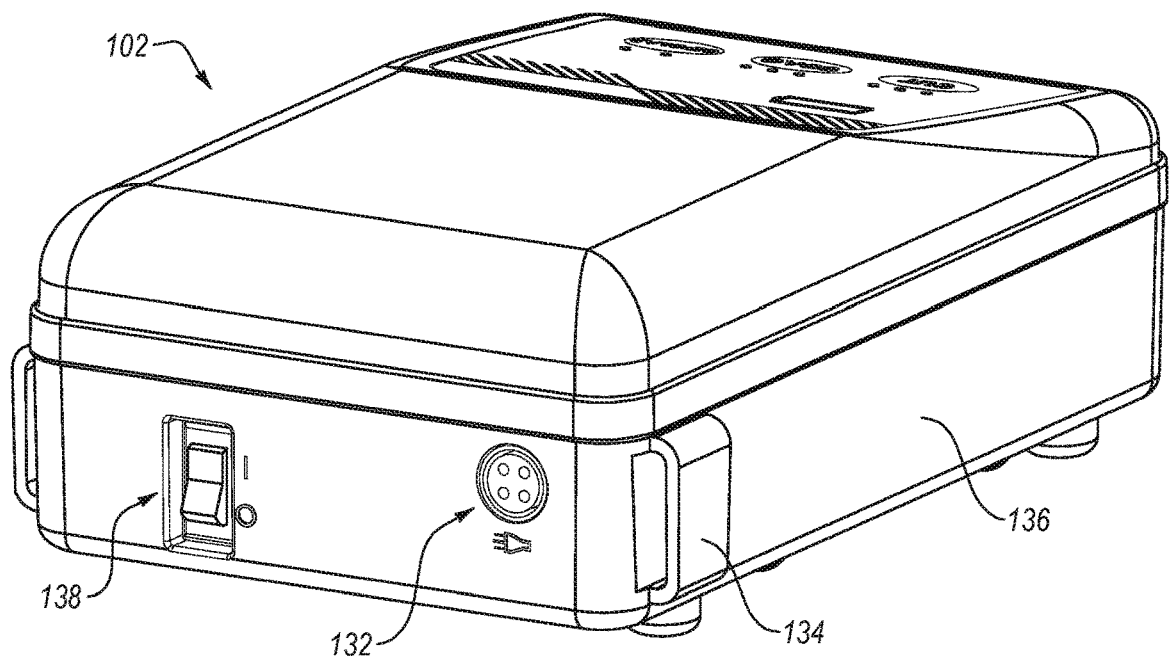
FIG. 2 illustrates a rear perspective view of an exemplary electrosurgical wave generator for use with the electrosurgical system of FIG. 1.

In some embodiments, the battery used to power the wave generator 102 may be rechargeable. In such embodiments, the wave generator 102 may have a battery recharging unit incorporated therein. As shown in FIG. 2, the wave generator 102 may include a connector 132 that allows for the wave generator 102, and particularly the incorporated recharging unit, to be connected to a power source (e.g., A/C wall socket), to power the recharging unit to enable the incorporated battery to be recharged. In other embodiments, the wave generator 102 may not include a recharging unit. Rather, the wave generator 102 may be connected to an external recharging unit (via the connector 132 or another connector) in order to recharge the incorporated battery.

As discussed elsewhere herein, the wave generator 102 may utilize certain circuit efficiencies (e.g., use the same circuit structure for multiple operation modes) and componentry (e.g., planar transformers). Such circuit efficiencies and components can limit the size and weight of the wave generator 102, thereby making the wave generator 102 more readily portable than traditional electrosurgical generators. For instance, using a single circuit structure for multiple operation modes can eliminate the need for multiple circuit structures typically included in multi-operation mode electrosurgical generators. This efficiency in circuit structure may also have the added benefit of reducing costs and complexity.

In some embodiments, the size and weight of the wave generator 102 can be sufficiently limited so that the wave generator 102 can be readily carried in a user's hand, medical bag, ruck sack, or the like. Similarly, the size and weight of the wave generator 102 may be sufficiently limited to allow for the wave generator 102 to be worn by a user (via a shoulder strap, belt, etc.). As shown in FIGS. 1-2, for instance, the wave generator 102 may include one or more attachment points 134 to which a shoulder strap may be attached or through which a user's belt may pass.

In some embodiments, the wave generator 102 may have a length, a width, and a height, or combinations thereof that facilitate ready transport by allowing the wave generator 102 to be easily carried, warn, or fit in a relatively small container or bag. In some embodiments, for instance, the wave generator 102 has a length of about 6 inches, about 8 inches, or about 10 inches, or within a range between about 5 inches to about 12 inches. Similarly, the wave generator 102 may have a width of about 5 inches, about 6 inches, about 8 inches, or about 10 inches, or within a range between about 4 inches to about 12 inches. Likewise, the wave generator 102 may have a height of about 2 inches, about 2.5 inches, about 3 inches, about 5 inches, about 7 inches, or about 9 inches, or within a range between about 2 inches to about 12 inches.

Regardless of the specific length, width, and height combinations available for the wave generator 102, the wave generator 102 may have a volume that is limited enough to facilitate ready transport thereof. For instance, the wave generator 102 may have a volume of about 60 cubic inches, about 100 cubic inches, about 120 cubic inches, or about 150 cubic inches, or within a range of between about 50 cubic inches and about 300 cubic inches, or within a range of between 50 cubic inches and about 750 cubic inches.

Similarly, the weight of the wave generator 102 can be sufficiently limited so that the wave generator 102 can be readily carried or transported without excessive effort. For instance, in some embodiments, the wave generator 102 may weigh about 2 pounds, about 3.5 pounds, about 5 pounds, about 7 pounds, or about 10 pounds. In some embodiments, the wave generator 102 may have a weight within a range between about 1 pound and about 3 pounds, between about 2 pounds and about 5 pounds, between about 3 pounds and about 7 pounds, or between about 1.5 pounds and about 6 pounds.

As noted above, the portable nature of the wave generator 102 may allow for use in non-traditional settings for surgical operations, including the outdoors. Accordingly, the wave generator 102 may be weatherized and/or ruggedized to ensure the wave generator 102 is operable in various conditions. For instance, the shell or casing 136 of the wave generator 102 may be formed of rigid and/or water resistant materials, such as plastic. Additionally, the seams of the shell 136, the electrical connections 120, 122, 124, 132, and the like, can include seals or other mechanisms to prevent the ingress of water, fluids, dirt, dust, organisms, and the like.

The wave generator 102, and particularly the shell 136 and other externally exposed surfaces or components, can be formed of, coated with, or otherwise include antibacterial or antimicrobial materials, such as silver ions, aluminum oxide, titanium dioxide, or other catalytic particles, chemical antibacterial components, and the like. Unlike traditional electrosurgical generators that are used in sterile operating room type settings, the wave generator 102 may be used in a variety of non-sterile settings. Accordingly, antibacterial or antimicrobial materials may be used to limit or prevent bacteria or microbes from entering, contaminating, or growing on the wave generator 102.

Activation/Indicators

As shown in FIG. 2, the wave generator 102 may include a power switch 138 that can be used to turn the wave generator 102 on and off. When the wave generator 102 is powered off, battery life may be preserved and inadvertent activation of a connected instrument (e.g., instruments 104, 106) may not result in injury.

In addition or as an alternative to turning the wave generator 102 on via a power switch (e.g., power switch 138), the wave generator 102 may be turned on and/or activated by electrically connecting an instrument (e.g., instruments 104, 106) and/or a return electrode (e.g., return electrode 108) to one or more of the electrical connections 120, 122, 124. For instance, connecting the connector 128 of instrument 106 to electrical connection 122 may turn on or activate the wave generator 102. Similarly, connecting the connector 126 of instrument 104 to electrical connection 120 may turn on or activate the wave generator 102. In some embodiments, when a monopolar instrument (e.g., instrument 104) is connected to the wave generator 102, the wave generator 102 may also require a return electrode (e.g., return electrode 108) to be connected to the wave generator 102 before the wave generator 102 will turn on or be activated. Requiring a monopolar instrument and a return electrode to be connected before the wave generator 102 turns on or is activated may help to ensure that a user does not attempt to use a monopolar electrosurgical instrument without a return electrode.

To help preserve battery life, the wave generator 102 may also be equipped with a sleep mode. The sleep mode may be used/activated when the wave generator 102 is turned on (e.g., either via power switch 138 or connection of an instrument (104, 106)) but has not been used for a predetermined amount of time. For instance, if the wave generator 102 has been turned on, but a connected instrument (e.g., instruments 104, 106) has not been activated in more than the last given period of time (e.g., the last about 2 minutes, about 5 minutes, about 10 minutes), the wave generator 102 may (automatically) enter a sleep mode. In the sleep mode, some or all of the electrical components may be deactivated.

In some embodiments, the wave generator 102 may wake from the sleep mode simply upon activation of a connected instrument (e.g., instruments 104, 106). For instance, if the wave generator 102 has entered the sleep mode as a result of non-use for a given period of time, a user may simply activate a connected instrument (e.g., instrument 104, 106) in order to wake the wave generator 102 from the sleep mode. As a result, the user does not have to use the power switch 138 or disconnect and reconnect the instrument in order to turn on/activate the wave generator 102. Thus, a user may not even know that the wave generator 102 was in a sleep mode.

The wave generator 102 may track certain information about the use thereof. By way of example, the wave generator 102 may track the total amount of time the wave generator 102 has been used/activated since the last complete or partial battery charge. Similarly, the wave generator 102 may track the amount of time the wave generator 102 has been used/activated for a particular procedure. The wave generator 102 may also track output parameters (e.g., voltage, current, power, etc.) for a given period of time or procedure.

The wave generator 102 may provide indicators to a user about the use and/or status thereof. For instance, as shown in FIG. 1, the wave generator 102 may include a battery indicator 140 that communicates the condition of the internal battery (e.g., level of charge used/remaining, etc.). The battery indicator 140 may be a pictorial or digitally visible indicator or may be an audible indicator. In some embodiments, the battery indicator 140 may provide a warning to the user when the battery is running low. For instance, the battery indicator 140 may flash or make an audible sound to indicate that the battery needs to be recharged or the wave generator 102 needs to be plugged in.

The wave generator 102 may also have various mode indicators 142 that identify which mode (e.g., cut, coagulation, bipolar) the wave generator 102 is operating in. In addition to identifying which mode the wave generator 102 is operating in, the mode indicators 142 may also indicate an output level within the operational mode. For instance, the mode indicators 142 may indicate that the wave generator 102 is operating in a cutting mode as well as whether the wave generator 102 is operating in a "low," "medium," or "high" cutting mode.

In some embodiments, the wave generator 102 may provide visual or audible indicators regarding the use thereof. For instance, when performing certain types of procedures, the wave generator 102 may provide a visual or audible indication that the procedure has been started and/or is complete. By way of example, in connection with an auto start and/or auto stop feature (discussed elsewhere herein), the wave generator 102 may provide a visual or audible indication that the procedure (or generator output) has started and/or stopped. Such a visual or audible indication may indicate to the user, among other things, that the instrument (e.g., instruments 104, 106) is actively applying electrical energy to tissue, that the instrument has been or may be deactivated, or that the procedure may proceed to another step.

Incorporated Return Electrode

Figure 3:
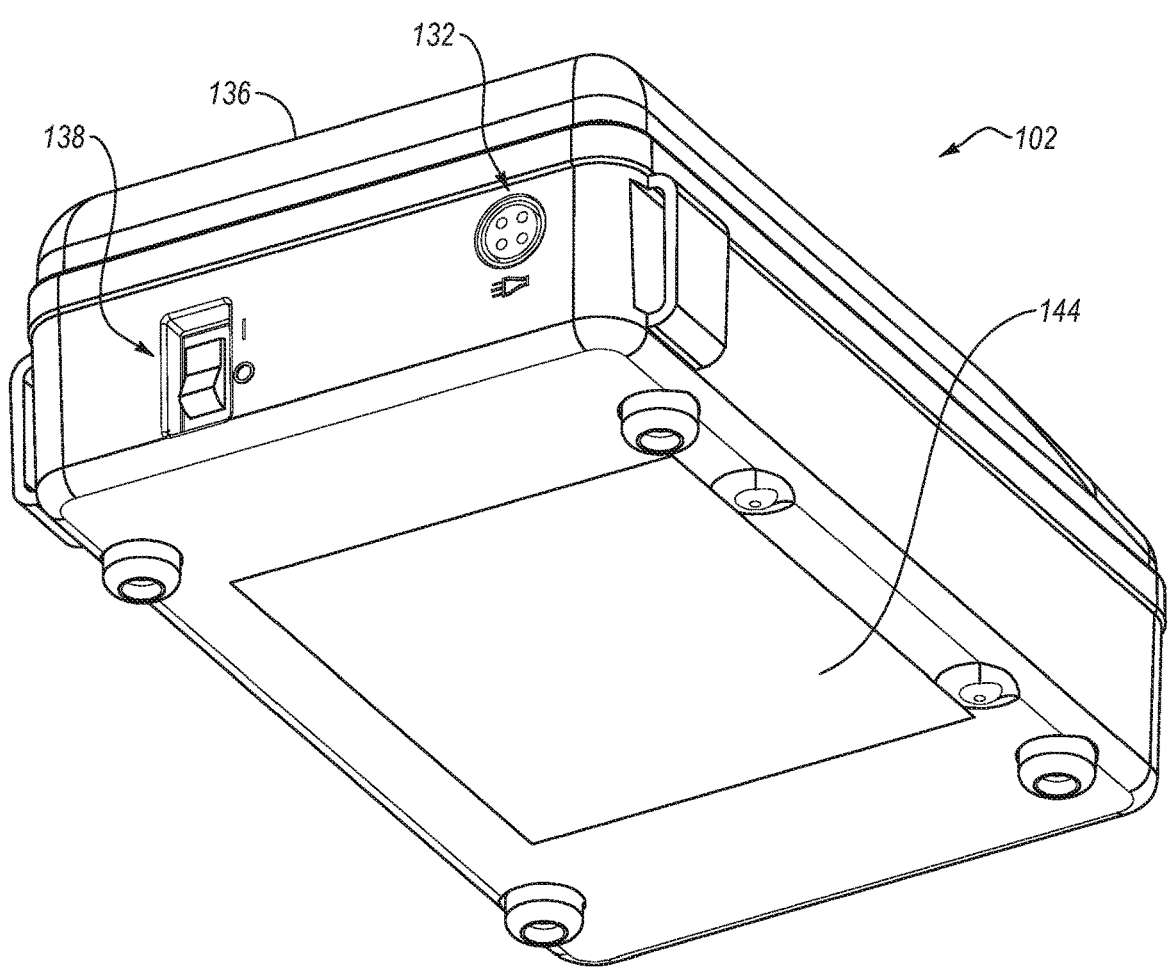
FIG. 3 illustrates bottom perspective view of an exemplary electrosurgical wave generator for use with the electrosurgical system of FIG. 1.

In addition or as an alternative to using return electrode 108, the wave generator 102 may include an incorporated return electrode. In FIG. 3, for instance, a portion of the bottom surface of the wave generator 102 forms or has incorporated therein a return electrode 144. In some embodiments, the return electrode 144 may be a capacitive return electrode that capacitively couples a conductive element with the patient's tissue. In other embodiments, the return electrode 144 may be a resistive or conductive return electrode. The return electrode 144 may be electrically connected to the internal circuitry of the wave generator 102 such that electrical energy applied to a patient's tissue with a monopolar instrument (e.g., instrument 104) may be returned to the wave generator 102 via the return electrode 144. In use, the wave generator 102 may be set on or strapped to a patient during an electrosurgical procedure so that the incorporated return electrode 144 may make sufficient contact with the patient to enable electrosurgery to be safely performed.

In some embodiments, the incorporated return electrode 144 may be washable, sanitizable, and/or sterilizable such that the return electrode 144 may be reused. In other embodiments, however, the wave generator 102 may be a disposable unit such that the return electrode 144 does not need to be washable, sanitizable, and/or sterilizable. Some of the other structural features described herein may also enable the wave generator 102 to be a disposable or one-time use unit. For instance, the size, circuit efficiencies, and the like, as well as the relatively minimal cost associated therewith, may allow the wave generator 102 to be disposable.

Communication Capabilities

The wave generator 102 may also include hardware and/or software components that allow for data communication between the wave generator 102 and a separate computing device. For instance, in some embodiments, the wave generator 102 may include a communications port that enables a hardwire connection between the wave generator 102 and the separate computing device. In other embodiments, the wave generator 102 may include a wireless transceiver (Bluetooth, cellular, etc.) that enables wireless communication between the wave generator 102 and the separate computing device.

Regardless of the specific type of communication components used, data may be communicated between the wave generator 102 and the separate computing device. Such data communication may include maintenance of or software updates for the wave generator 102. The data communication may also include uploading of data from the wave generator 102 to the separate computing device. The uploaded data may include information about the use history of the wave generator 102, and the like.

Furthermore, the data communication may allow for the separate computing device to control the settings or customize the modes, settings, and/or programs of the wave generator 102. Allowing for the remote control of the wave generator 102 may be useful for a variety of reasons and in various circumstances. By way of example, in a military setting with an in the field medic that has some, but not extensive medical training, a remotely located doctor could control the settings of the wave generator 102 via a separate computing device while providing guidance to the medic via radio or telephone communication on how to perform the surgical procedure.

Cutting Mode

Some embodiments of the wave generator 102 can include an electrosurgical cutting mode that is configured to utilize pulse width modulation (PWM) at the output. In particular, the wave generator 102 can utilize PWM to generate a constant voltage peak level at a working surface of an associated electrode tip (e.g., a cutting or knife edge of the electrode tip 110), while varying the pulse width to achieve the desired cutting characteristics. In an alternate embodiment, the cutting mode can comprise amplitude control without PWM to control the power and voltage at the working surface of the associated electrode tip.

For example, when cutting through tissue, the wave generator 102 can determine the impedance of tissue that is being cut. Upon determining that a high impedance tissue (e.g., fibrous tissue) has been reached, the wave generator 102 can increase the duty cycle of the PWM signal. Increasing the duty cycle may cause the power to be applied to the working surface of the electrode tip for a longer period of time. The increased duration of the applied voltage, or power, to the working surface of the electrode tip can increase the cutting ability of the electrode tip. In contrast, when cutting through low impedance tissue, the wave generator 102 can utilize a lower duty cycle that uses less power and applies less heat to tissue.

Figure 4:
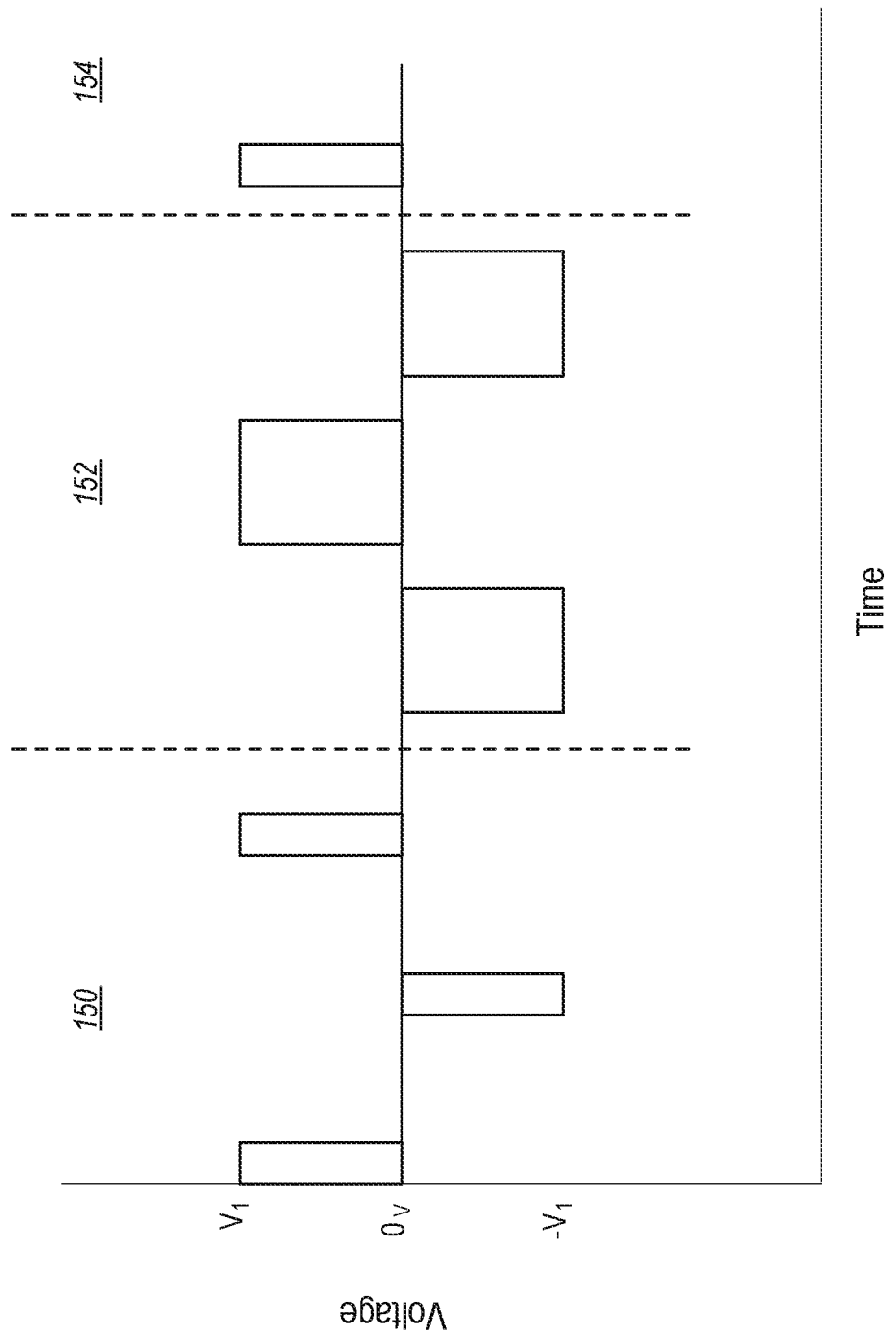
FIG. 4 illustrates an exemplary voltage-over-time graph of a PWM output produced by an electrosurgical wave generator according to an example cutting mode of the present disclosure.

FIG. 4 depicts a voltage-over-time graph of an exemplary PWM output at a working surface of an electrode tip as produced by the wave generator 102 in one embodiment of the present disclosure. For example, during time period 150, the working surface may be cutting through a low impedance tissue. As depicted, in response to the low impedance tissue, the wave generator 102 can utilize a low duty cycle. In contrast, during time period 152, the wave generator 102 may detect a high impedance tissue. In response to detecting the high impedance tissue, the wave generator 102 can increase the duty cycle. The voltages during time period 152 may comprise substantially the same voltage levels as the pulses during time period 150. Further, during time period 154, the wave generator 102 may detect a low impedance tissue and return to a duty cycle similar to that of time period 150.

As such, embodiments of the present disclosure may increase cutting ability through high impedance tissues by increasing the relative amount of time that a voltage is applied to the tissue. Additionally, at least one embodiment of the present disclosure changes the duty cycle of voltage pulses at the working surface, without substantially changing the voltage of the pulses. Accordingly, embodiments of the present disclosure can automatically adapt to different cutting needs without increasing the voltage.

One will understand that the graph depicted in FIG. 4 is merely exemplary and that the voltages, pulse shapes, and frequencies are depicted for the purposes of clarity and discussion and do not necessary reflect actual outputs. For example, in various embodiments, the wave generator 102 may operate at a frequency of 530 KHz. Similarly, in various embodiments, the generally square pulses may comprise rounded edges. Further, in at least one embodiment, pulse shapes other than generally square pulses may be used.

Typical wave generators use sinusoidal waves that can be amplitude modulated in order to adjust output signals. As noted herein, the wave generator 102 can employ generally square waves that can be pulse width modulated to adjust the output signals. The wave generator 102 may also use sinusoidal waves that can be amplitude adjusted, similar to typical generators. Additionally, in some embodiments, the generally square waves used by wave generator 102 may also be amplitude modulated to adjust the output signals. Thus, the circuitry of the wave generator 102 may have the flexibility to use either sinusoidal wave or generally square waves, which may be amplitude modulated or pulse width modulated.

In at least one embodiment, the wave generator 102 may comprise various pre-defined power levels to meet the particular needs of a given surgery. The various power levels (e.g., low, medium, high) may each be associated with a particular power level and/or voltage. For example, in at least one embodiment, a low setting may be associated with about 10 watts output, medium with about 30 watts output, and high with about 40 watts output. Additionally, in at least one embodiment, each higher setting can respectively increase the voltage of the PWM pulses. As such, a high setting can comprise a higher voltage than a low setting.

In some embodiments, it may be desirable to limit the wattage output to below certain desired thresholds. Limiting the output wattage to below certain desired thresholds can provide various benefits. For instance, if the output wattage is maintained below certain thresholds (e.g., below about 49 or 50 watts), contact quality monitoring systems may not be needed. Contact quality monitoring systems are typically used to ensure that there is sufficient contact between a patient and a return electrode. Insufficient contact can result in a patient burn when using typical higher output wattage electrosurgical generators. In contrast, when the output wattage is limited, the risk for a patient burn is reduced or eliminated, thereby reducing or eliminating the need for contact quality monitoring systems.

In at least one embodiment, the power level can also be associated with baseline duty cycles of the PWM pulses. For example, the low setting may be associated with a fifteen percent duty cycle, the medium setting may be associated with a thirty percent duty cycle, and the high setting may be associated with a fifty percent duty cycle. Though the duty cycles at any power level can be adjusted to meet the specific tissue conditions, the baseline duty cycles may bias the PWM such that the low level setting increases its duty cycle slower than the high level setting. Additionally, in at least one embodiment, the low level duty cycle may be biased to maintain a high duty cycle for a shorter time than the medium setting or high setting would maintain the same duty cycle.

Bipolar Mode

Some embodiments of the wave generator 102 can also or alternatively include a bipolar mode that is configured to apply constant current to an output. In particular, the bipolar mode can operate by outputting a particular current and monitoring a detected impedance at the output to determine whether a procedure is complete. In at least one embodiment, once a specific impedance threshold it detected, the bipolar mode can deactivate or otherwise indicate that the procedure is complete.

Thus, in some embodiments, the wave generator 102 may provide an auto start and/or auto stop feature. In an auto start feature, the wave generator 102 may apply a desired output (e.g., constant current) once an instrument (e.g., instrument 106) has been activated and touched to patient tissue. In an auto stop feature, the wave generator 102 may change or discontinue the output after a specified time period or upon a change in conditions. For instance, the wave generator 102 may change or discontinue the output upon a predetermined change in tissue impedance, voltage, power, or the like.

In various embodiments, the bipolar mode can comprise various setting levels that indicate a desired power level at the output (e.g., 25 watts or 50 watts). As such, in at least one embodiment, the output of a bipolar mode is controlled such that the wave generator 102 attempts to maintain a constant current output or constant power output. In at least one embodiment, the wave generator 102 can maintain the desired output current or power through amplitude modulation of the voltage. In at least some embodiments, the wave generator 102 can maintain the desired output current or power through pulse width modulation of the output signal or generally square waveform.

Figure 5:
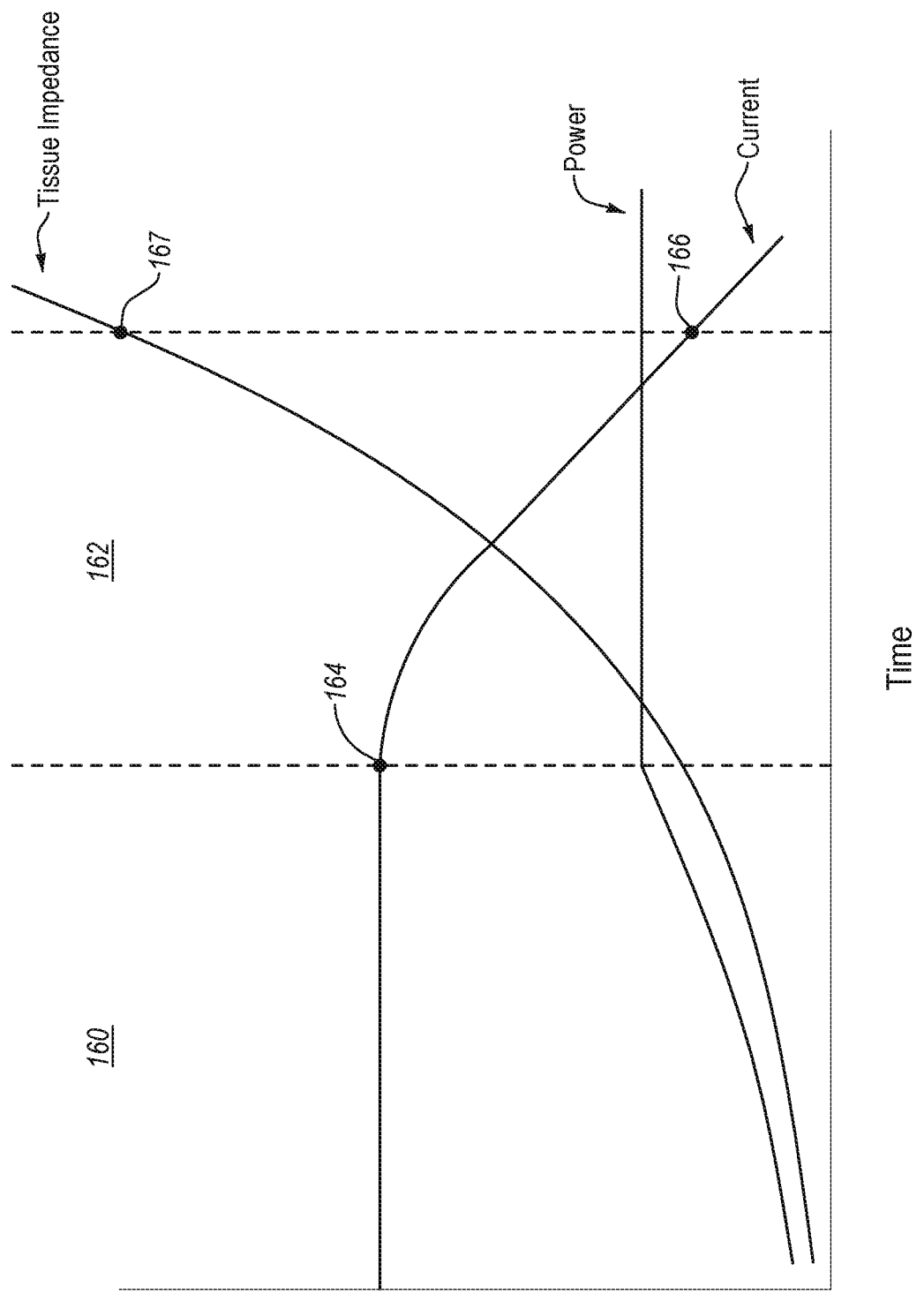
FIG. 5 illustrates a time based relationship of current, power, and measured tissue impedance graph of an exemplary bipolar output produced by an electrosurgical wave generator according to an example bipolar mode of the present disclosure.

For example, FIG. 5 depicts a time based relationship of current, power, and measured tissue impedance of an exemplary bipolar procedure. As depicted, in at least one embodiment, the bipolar mode initially outputs a generally constant current over an initial time period and impedance range 160. Over time as the tissue contracts, the impedance of the tissue increases, resulting in an increase in power as current remains constant. During a second phase, shown by time period 162, the output is changed to a generally constant power output, which may eventually lead to a rapid decrease in current (as illustrated between 164 to 166) in order to maintain the power level as the tissue impedance increases. In at least one implementation, the rapid decrease in current within region 162 leads to the detection of a threshold impedance 167, which can indicate the completion of the procedure.

In some embodiments, the threshold impedance may be about 100 ohms. In other embodiments, the threshold impedance may be in a range from between about 50 ohms to about 300 ohms, or in a range from between about 50 ohms to about 1000 ohms. The threshold impedance may vary based on certain factors. For instance, the type of tissue or the amount of tissue (e.g., grasped between bipolar forceps) to which the current is applied may affect the threshold impedance value, as well as the amount of time the energy is applied to the tissue.

For instance, a small amount of tissue (grasped between bipolar forceps) may start with a relatively high impedance compared to a larger amount of tissue, and the impedance of the small amount of tissue may increase more rapidly (compared to a large amount of tissue) to a relative high or threshold impedance level. In contrast, a large amount of tissue (grasped between bipolar forceps) may start with a relatively low impedance (compared to a small amount of tissue), and the impedance level of the large amount of tissue may increase more slowly (compared to a small amount of tissue) to a relatively high or threshold impedance level. In some instances, such as with a type of tissue or an amount of tissue that starts with a relatively high impedance level, the threshold impedance level may be lower than a threshold impedance level of a different type of tissue or a smaller amount of tissue.

In at least one embodiment, applying constant current over a time period may function to slowly warm tissue and cause the tissue to contract. In contrast, conventional bipolar modes may comprise high levels of initial current that quickly drop. The high levels of current may cause charring and other issues that can be mitigated by embodiments of the present disclosure.

Additionally, in at least one implementation, the bipolar mode can be implemented within the wave generator 102 by the same circuit used to implement the cutting mode. For example, in at least one embodiment, the bipolar mode operates at a constant 50% PWM duty cycle. Accordingly, the amplitude of the voltage can be varied while maintaining a constant duty cycle. Sharing the circuit between at least these two modes may significantly reduce the cost of the wave generator 102 and, as discussed elsewhere herein, significantly shrink the size/weight of the wave generator 102.

Coagulation Mode

In some embodiments, the wave generator 102 can include a coagulation mode that utilizes a flyback circuit for controlling the amount of power applied to the output. For example, in at least one implementation, the flyback circuit can be used to provide a constant power output without regard to the voltage applied to the output load or the impedance of the output load.

Typically, coagulation modes, as the name indicates, are used to coagulate blood during a surgical procedure. Conventional coagulation systems rely upon extremely high voltages in the range 4,000 volts peak-to-peak to achieve the desired coagulation effect. Maintaining the proper voltage and power levels and accounting for the changing impedance of the output can require significant monitoring overhead.

In at least one embodiment, the wave generator 102 utilizes a flyback circuit in such a way that constant power output can be achieved without having to monitor changing voltages or impedance. For example, the wave generator 102 can control the amount of power being applied to the primary side of the transformer within the flyback circuit. The control may comprise amplitude modulation, current modulation, or any other form.

Once the power is applied to the primary side of the transformer, the secondary side of the flyback circuit can store the energy within the inductor and release the energy as a pulse to the load (i.e., tissue). Because the power applied to the primary side of the flyback circuit will be substantially equal to the power stored and outputted by the secondary side of the flyback circuit, a substantially constant power is applied by the wave generator 102 with a significantly higher voltage than the voltage applied to the primary side of the flyback circuit.

As such, in at least one embodiment, the flyback circuit allows the coagulation mode to be used without requiring any monitoring of voltage applied to the tissue or impedance at the output. The flyback circuit ensures that the proper, constant power level is applied to the tissue without regard to the voltage or impedance at the load.

Additionally, in at least one embodiment, the wave generator 102 may comprise a gate that functions to control pulse timing and crest factor at the output. In particular, in at least one implementation, the gate can be connected to the PWM controller described above. In coagulation mode, the PWM controller may operate at a constant duty cycle. The gate can further be used to determine which pulses are passed through to the output. Additionally, the gate can be used to control the crest factor of the pulses.

Also, in at least one embodiment, crest factor adjustment in coagulation mode can be used to improve the effect and efficiency of activation for customized electrode geometries. An increase in the crest factor may improve the coagulation effect when using an electrode with an edge geometry that is shaped to have a working surface generally between about 0.0254 mm and about 0.1270 mm or between about 0.076 mm and about 0.1270 mm. This is in comparison to a working surface of a conventional unsharpened electrode tip (with a thickness of about 0.33 mm), which works best in coagulation mode with a lower crest factor. In some embodiments, crest factors may range from a low crest factor value of about 5 to a high crest factor value of about 12. Other electrode geometries may have associated crest factor adjustments that can be made for effective coagulation activation.

Circuit Efficiencies

In at least one embodiment, the wave generator 102 can implement a cutting mode, a bipolar mode, and a coagulation mode all within the same circuit structure. For example, the circuit may comprise a PWM controller that can be used as described above for the cutting mode. When the wave generator 102 is utilized in the bipolar mode or coagulation mode, the PWM controller can be set to a constant duty cycle—such that the output is no longer PWM controlled.

Figure 6:
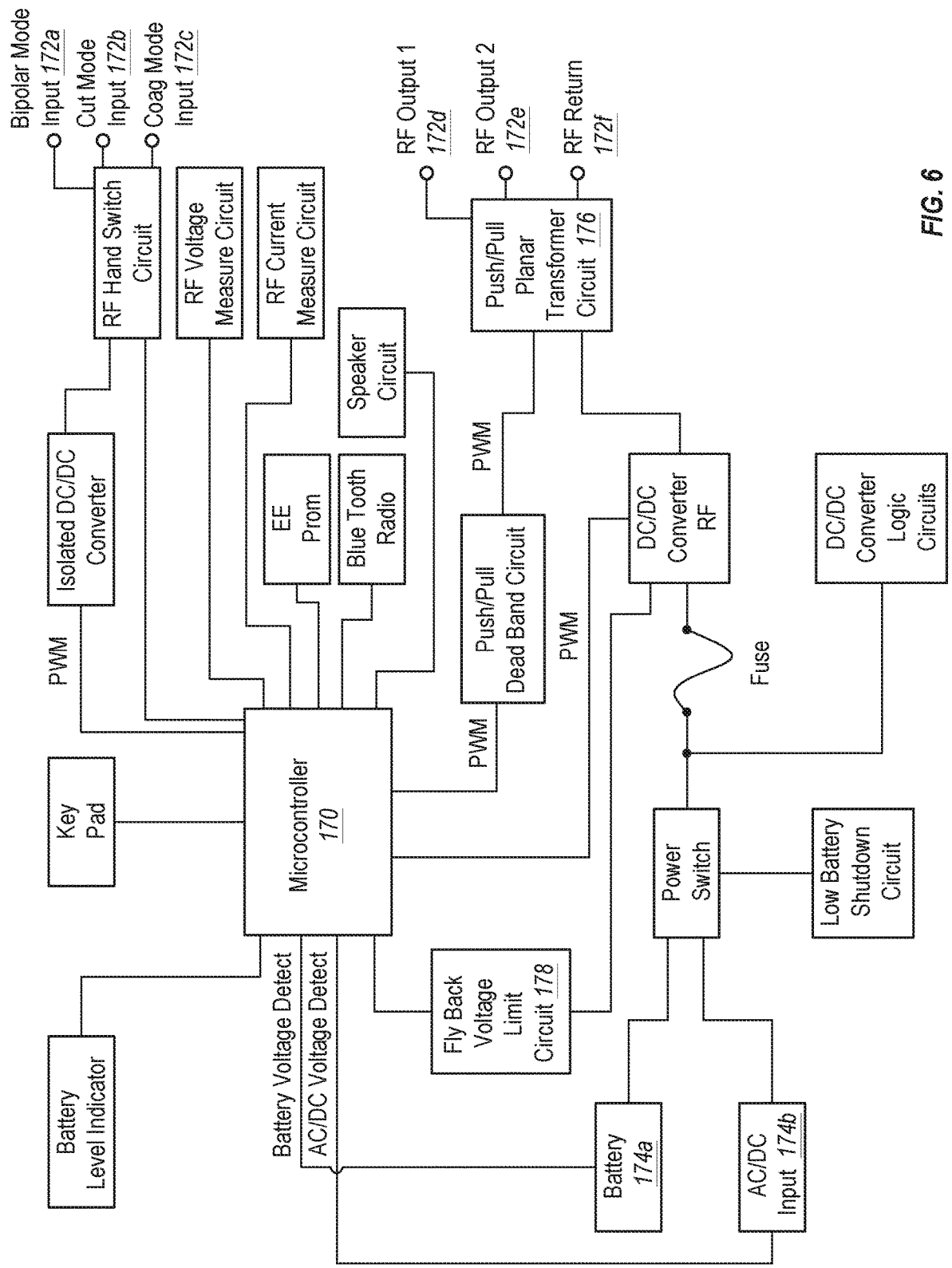
FIG. 6 illustrates a schematic diagram of an implementation of a circuit for a wave generator usable with the electrosurgical system of FIG. 1.

FIG. 6 depicts a schematic diagram of an implementation of a circuit for a battery-powered, portable electrosurgical wave generator (e.g., wave generator 102). In particular, the schematic depicts a microcontroller 170 in communication with various components and modules within the wave generator. As shown, in at least one implementation, the various input/output ports 172(a-f) are all in communication with the same microcontroller 170 and the same power sources 174(a-b).

Similarly, in at least one implementation, a planar transformer 176 can be utilized to feed at least a portion of the outputs 172(c-f). For example, the planar transformer 176 may comprise multiple taps 172(c-f) that each feed a particular output. Additionally, in at least one implementation, an input to the planar transformer 176 may be in communication with a flyback circuit 178, described above with respect to the coagulation mode.

In various embodiments of the present disclosure, the components and methods described herein can be implemented using any combination of analog or digital modules. For example, in at least one implementation, the wave generator 102 can be controlled using digital processing. In contrast, in at least one embodiment, the wave generator 102 can be completely analog.

Wave Generator and Instrument Combinations

The performance capabilities (e.g., cutting, coagulation, and bipolar modes) of the wave generator 102 may be suited for or useful with particular types of electrosurgical instruments. For instance, the cutting mode described herein may be particularly suited for use with or provide enhanced cutting performance when used with an electrode tip that has a shaped, tapered, or sharpened working surface (referred to hereinafter as a "shaped working surface"). A shaped working surface concentrates the electrical energy transferred from the electrode tip to the patient's tissue. The concentrated electrical energy reduces the amount of extraneous charge loss into surrounding tissue, thereby reducing the amount of necrotic damage in the tissue surrounding the incision site.

Referring back to FIG. 1, the electrode tip 110 may include a shaped working surface 168 that can facilitate efficient and concentrated transfer of the electrical energy to the patient tissue. On an irregularly shaped conductor, charge tends to accumulate at locations where the curvature of the surface is greatest; that is, at sharp or tapered points or edges. By shaping or sharpening the working surface 168 of the electrode tip 110, the charge is concentrated along a much smaller surface area or region. As a result, the electrical energy is focused into a tighter arrangement, which reduces extraneous charge loss in tissue that is not in close proximity to the shaped working surface 168.

The shaped working surface 168 of the electrode tip 110 does need not to be sharply pointed; it need only be shaped (sharpened) to concentrate energy transfer to the degree desired for optimum cutting. For instance, the efficacious characteristics may begin to be significantly observed when the dimension (i.e., width) of the shaped working surface 168 is generally between about 0.0254 mm and about 0.1270 mm or between about 0.076 mm and about 0.1270 mm. In some embodiments, the shaped working surface 168 may have a dimension of about 0.0254 mm, about 0.076 mm, about 0.01016 mm, or about 0.1270 mm.

A conventional unsharpened electrode tip has a working surface thickness of about 0.33 mm and in a typical cutting mode may utilize a power setting nearing 50 watts. In contrast, an electrode tip with a shaped working surface 168 may quickly cut through tissue at less than 20 watts, a power setting of 50% less than that required for typical unsharpened electrode tips. A shaped working surface 168 may also allow for the PWM cutting mode described herein to use shorter duty cycles than a typical unsharpened electrode tip to cut through similar tissue. Additionally, electrode tips with a shaped working surface 168 may also cut more rapidly with less resistance, less eschar production, less thermal necrosis, and improved operator control.

Power requirements for shaped electrodes when compared with conventional electrodes may differ considerably when PWM is employed. The depth of tissue cut, the type of tissue, the length of the electrode, electrode shape, and other factors may affect the power requirement. Typical power reduction for shaped electrodes vs. conventional electrodes may be in the range of about 40% to 60%. Depending on depth of cut, tissue type, incision location, electrode length and shape, etc., the power reduction range may be from about 10% to 90%.

In some embodiments, the size and/or other configuration of the electrode tip 110 in combination with the PWM cutting mode described herein may facilitate the performance of procedures in which a high level of precision is desired. For instance, in at least some embodiments, the electrode tip 110 includes (i) one or more major surfaces (e.g., a first major surface and a second major surface opposite the first major surface); (ii) one or more longitudinal side edges (e.g., disposed at least partially between the first major surface and the second major surface); and/or (iii) a cross-sectional area (e.g., disposed at least partially between the first major surface and/or the second major surface and/or the one or more longitudinal side edges).

In at least one embodiment, the thickness of the longitudinal side edge(s) can be greater than about 0.01 inches (0.254 mm). When a longitudinal side edge has a thickness greater than about 0.01 inches, the longitudinal side edge can form or include two or more longitudinal cutting edges, and/or the body can comprise a cross-sectional area-to-number of longitudinal cutting edges ratio that is less than or equal to about 0.0004 square inches per longitudinal cutting edge ($in^2/E$).

In one or more other embodiments, the longitudinal side edge(s) can have a thickness that is less than or equal to about 0.01 inches. When a longitudinal side edge has a thickness less than or equal to about 0.01 inches, the longitudinal side edge can form or include one longitudinal cutting edge, and/or the body can comprise a cross-sectional area-to-number of longitudinal cutting edges ratio that is less than or equal to about 0.000150 square inches per longitudinal cutting edge ($in^2/E$).

In one or more other embodiments, the electrode tip 110 can include one or more longitudinal side edges that have a thickness that is less than or equal to about 0.01 inches (each comprising one longitudinal cutting edge) and one or more longitudinal side edges that have a thickness that is greater than about 0.01 inches (each comprising two or more longitudinal cutting edges). When an embodiment includes a hybrid of longitudinal side edge(s) having thickness(es) less than or equal to about 0.01 inches and longitudinal side edge(s) having thickness(es) greater than about 0.01 inches, the body of the electrode can comprise a cross-sectional area-to-number of longitudinal cutting edges ratio that is less than or equal to about 0.001 square inches per longitudinal cutting edge (in²/E).

Figure 7:
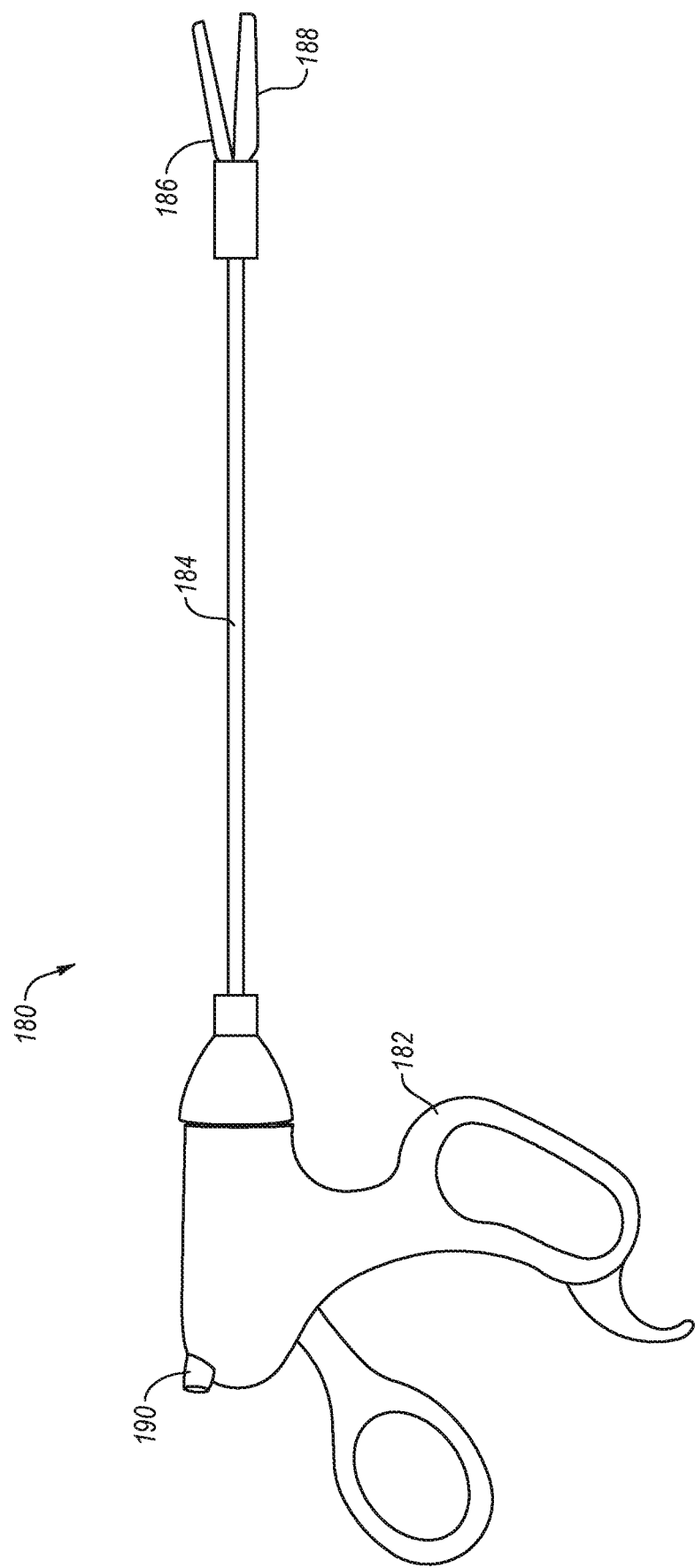
FIG. 7 illustrates an example vessel sealing instrument.

A vessel sealing instrument is another type of electrosurgical instrument that may be particularly suited for use in combination with the wave generator 102. FIG. 7 illustrates an example vessel sealing instrument 180 that may be used in conjunction with the wave generator 102. The vessel sealing instrument 180 includes a handle 182, an elongated shaft 184 extending from the handle 182, and a pair of jaws 186, 188 at the opposing end of the elongated shaft 184. The vessel sealing instrument 180 also includes an input 190 for receiving/returning electrical energy from an electrosurgical wave generator (e.g., wave generator 102) via a wire or other electrical conductor. The electrical energy may be used to, among other things, seal vessels or cut tissue that is between the jaws 186, 188.

The handle 182 may be designed such that squeezing a lever portion of the handle 182 toward another part of the handle 182 activates one or both of the jaws 186, 188. This activation may lower the jaw 186 onto or towards the jaw 188, or vice versa. Additionally or alternatively, squeezing the lever of the handle 182 may initiate the flow of electrical energy to one or both of the jaws 186, 188. In other cases, the handle 182 (or another part of the instrument 180) may include a separate switch or button that initiates the flow of electrical energy to one or both of the jaws 186, 188. In still other cases, a switch mechanism, such as a foot switch, may be used to initiate the flow of electrical energy to one or both of the jaws 186, 188.

A vessel sealing instrument (e.g., instrument 180) may be particularly useful when used in conjunction with the coagulation or bipolar modes described herein. For instance, a user may use the vessel sealing instrument 180 to grasp a blood vessel between the jaws 186, 188. The coagulation or bipolar mode may then be used to communicate electrical energy to the grasped blood vessel in order to heat the blood vessel. Heating of the blood vessel results in the denaturing of the collagen and elastin found in the blood vessel walls. After sufficient denaturing, the flow of electrical energy to the jaws 186, 188 (and thus to the blood vessel) is turned off, allowing the blood vessel to begin cooling. As the blood vessel cools, the elastin and collagen in the blood vessel walls—which are now in compressed contact—bond sealing them together and closing the vessel.

During the vessel sealing procedure, the jaws 186, 188 may act as a clamp to hold the opposing sides of the blood vessel wall together. The clamping force may be applied and/or maintained manually by moving and/or holding the lever portion of the handle 182. Alternatively, the vessel sealing instrument 180 may include a mechanical or electro-mechanical mechanism that maintains the clamping force until the vessel sealing procedure is completed. The mechanical or electro-mechanical mechanism may be configured to release the clamping force after a predetermined period of time (e.g., 5 seconds, 10 seconds, 15 seconds, 30 seconds), upon a user input (moving the lever portion of the handle 182), or in response an electrical signal (e.g., from the wave generator 102).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical wave generator for performing electrically driven medical procedures, the electrosurgical wave generator comprising:
    a housing;
    a control unit disposed within the housing and that is configured to generate and control output signals to a monopolar electrosurgical instrument or a bipolar electrosurgical instrument;
    a first electrical connection associated with the housing and configured to have the monopolar electrosurgical instrument selectively connected thereto;
    a second electrical connection associated with the housing and configured to have the bipolar electrosurgical instrument selectively connected thereto; and
    a third electrical connection associated with the housing and configured to have a return electrode selectively connected thereto,
    wherein an arrangement of the first, second, and third electrical connections relative to one another is configured to:
        enable simultaneous connection of the monopolar electrosurgical instrument to the first electrical connection and the return electrode to the third electrical connection; and
        prevent connection of the monopolar electrosurgical instrument to the first electrical connection and the return electrode to the third electrical connection when the bipolar electro surgical instrument is connected to the second electrical connection.

2. The wave generator as recited in claim 1, further comprising a pulse-width-modulation controller, the pulse width modulation controller being configured to drive the output signals in each of a coagulation mode and a cutting mode, wherein:
    in the cutting mode, the pulse width modulation controller is configured to vary duty cycles of the output signal based upon an impedance detected from the patient tissue that the electrode is cutting while maintaining a constant voltage peak level;
    the pulse-width-modulation controller is configured to increase a duty cycle associated with the output signals upon detection of a relatively higher impedance tissue; or
    the pulse-width-modulation controller is configured to decrease a duty cycle associated with the output signals upon detection of a relatively lower impedance tissue.

3. The wave generator as recited in claim 1, wherein the first and second electrical connections are positioned to allow for only one of the monopolar electrosurgical instrument or the bipolar electrosurgical instrument to be connected to the first or second electrical connections at a given time.

4. The wave generator as recited in claim 1, further comprising a battery incorporated therein, the output signals being generated solely from a voltage produced by the battery.

5. The wave generator as recited in claim 1, wherein the first and second electrical connections share at least one socket in common.

6. The wave generator as recited in claim 1, further comprising a wireless transceiver configured for transmitting or receiving data.

7. The wave generator as recited in claim 6, wherein the data includes one or more of software updates for the wave generator, changes to wave generator settings or modes, and data relating to the use of the wave generator.

8. The wave generator as recited in claim 1, wherein an outer shell or case of the wave generator comprises an integrated return electrode.

9. The wave generator as recited in claim 1, wherein the output signals are tailored for use with a surgical electrode that has a cross-sectional area-to-number of longitudinal cutting edges ratio that is less than or equal to 0.000150 square inches per longitudinal cutting edge.

10. The wave generator as recited in claim 1, wherein the output signals are tailored for use with a surgical electrode that has a cross-sectional area-to-number of longitudinal cutting edges ratio that is less than or equal to 0.001 square inches per longitudinal cutting edge.

11. The wave generator as recited in claim 1, wherein the output signals are tailored for use with a surgical electrode that has a cross-sectional area-to-number of longitudinal cutting edges ratio that is less than or equal to 0.0004 square inches per longitudinal cutting edge.

12. The wave generator as recited in claim 1, wherein, in a coagulation mode, a constant power output is maintained and a voltage level is able to fluctuate.

13. The electrosurgical wave generator as recited in claim 1, wherein the control unit that is configured to generate and control output signals performing surgical procedures in each of a cutting mode, a bipolar mode, and a coagulation mode, wherein the control unit is configured to automatically generate and control the output signals in one or more of the cutting mode, the bipolar mode, and the coagulation mode without requiring user input or manual adjustment to settings of the wave generator, the wave generator further comprising:
a pulse-width-modulation controller, the pulse width modulation controller being configured to drive the output signals within each of the cutting mode, the bipolar mode, and the coagulation mode, wherein, in the bipolar mode, the pulse-width-modulation controller is configured to drive an output signal during a first phase and during a second phase, the output signal having a constant current only during the first phase, and the output signal having a constant power only during the second phase, the first phase comprising an initial impedance range and an initial time period during which tissue impedance increases within the initial impedance range, the second phase comprising a higher impedance range and a subsequent time period during which tissue impedance increases within the higher impedance range, the pulse-width-modulation controller being configured to transition the output signal from the constant current to the constant power between the first and second phases when the tissue impedance increases from the initial impedance range of the first phase to the higher impedance range of the second phase.

14. The wave generator as recited in claim 13, wherein the pulse-width-modulation controller drives the output signals at a constant 50% duty cycle while functioning within the bipolar mode.

15. The wave generator as recited in claim 13, wherein the pulse-width-modulation controller drives the output signals at a constant duty cycle while functioning within the coagulation mode.

16. The wave generator as recited in claim 13, further comprising a planar transformer, wherein the planar transformer comprises multiple taps for different respective modes.

17. The wave generator as recited in claim 13, wherein, in the bipolar mode, the wave generator is configured to detect an impedance at the at least one surgical electrode to determine whether a procedure is complete, and wherein, when the wave generator detects that the procedure is complete, the wave generator is configured to deactivate the bipolar mode or provide an indication that the procedure is complete.

18. The wave generator as recited in claim 13, wherein the control unit allows for selective adjustment of one or more settings of the wave generator in order to adjust the output signals.

19. The wave generator as recited in claim 1, wherein:
the housing has a length, width, and height dimensions and a total volume that are limited to enable the wave generator to be carried and used in a non-operating room type setting, the housing comprising one or more attachment points configured to receive a strap or belt, the housing being configured to be strapped to a patient during an electrosurgical procedure;
the control unit being further configured to generate and control output signals to at least one surgical electrode for performing surgical procedures in each of a cutting mode, coagulation mode, and a bipolar mode, the control unit using a single circuit structure to generate the output signals for the cutting, coagulation, and bipolar modes; the wave generator further comprising:
a battery disposed within the housing, the output signals being generated solely from a voltage produced by the battery; and
the return electrode having a working surface configured to be placed in contact with the patient during a surgical procedure to enable the safe flow of electrical energy from the patient to the wave generator via the return electrode, the return electrode forming or covering a portion of only a bottom surface of the housing, such that the wave generator can be positioned on or strapped to the patient with the working surface of the return electrode in contact with the patient during the surgical procedure.

20. The wave generator as recited in claim 19, wherein the housing has the total volume of between about 50 cubic inches and about 750 cubic inches.

21. The wave generator as recited in claim 19, wherein the housing has the total volume of about 60 cubic inches, about 100 cubic inches, about 120 cubic inches, or about 150 cubic inches.

22. The wave generator as recited in claim 19, wherein the wave generator has a total weight of between about 1 pound and about 6 pounds.

23. The wave generator as recited in claim 19, wherein the wave generator has a total weight of about 2 pounds, about 3.5 pounds, about 5 pounds, about 7 pounds, or about 10 pounds.

24. The wave generator as recited in claim 19, further comprising a wireless transceiver configured for transmitting or receiving data.

25. The wave generator as recited in claim 19, wherein an output wattage of the wave generator is limited to about 49 watts or less.

26. The wave generator as recited in claim 19, wherein the housing comprises or is formed of weather resistant materials.

27. The wave generator as recited in claim 19, wherein the housing comprises, is formed of, or coated with antibacterial or antimicrobial materials.

28. An electrosurgical wave generator for performing electrically driven medical procedures, the electrosurgical wave generator comprising:
- a housing;
- a control unit disposed within the housing and that is configured to generate and control output signals to a monopolar electrosurgical instrument or a bipolar electrosurgical instrument;
- a first electrical connection associated with the housing and configured to have the monopolar electrosurgical instrument selectively connected thereto;
- a second electrical connection associated with the housing and configured to have the bipolar electrosurgical instrument selectively connected thereto, the second electrical connection comprising first and second receptacles; and
- a third electrical connection associated with the housing and configured to have a return electrode selectively connected thereto, the third electrical connection being positioned between the first and second receptacles of the second electrical connection,
- wherein the positioning of the second electrical connection between the first and second receptacles of the third electrical connection prevents the simultaneous connection of the return electrode to the third electrical connection and the bipolar electrosurgical instrument to the second electrical connection.

29. The wave generator as recited in claim 28, wherein the first electrical connection and the third electrical connection are arranged relative to one another to enable simultaneous connection of the monopolar electrosurgical instrument to the first electrical connection and the return electrode to the third electrical connection.

30. The wave generator as recited in claim 28, wherein the first electrical connection comprises a plurality of receptacles.

31. The wave generator as recited in claim 28, wherein the first electrical connection and the second electrical connection share at least one common receptacle.

32. The wave generator as recited in claim 31, wherein sharing the at least one common receptacle by the first electrical connection and the second electrical connection prevents the simultaneous connection of the monopolar electrosurgical instrument to the first electrical connection and the bipolar electrosurgical instrument to the second electrical connection.

\* \* \* \* \*